United States Patent [19]

Snell

[11] 4,041,157
[45] Aug. 9, 1977

[54] FUNGICIDAL PYRIMIDINE DERIVATIVES

[75] Inventor: Brian Kenneth Snell, Bracknell, England

[73] Assignee: Imperial Chemical Industries Limited, London, England

[21] Appl. No.: 608,331

[22] Filed: Aug. 27, 1975

Related U.S. Application Data

[60] Division of Ser. No. 114,079, Feb. 9, 1971, Pat. No. 3,906,094, which is a continuation-in-part of Ser. No. 624,126, March 20, 1967, abandoned.

[30] Foreign Application Priority Data

Mar. 31, 1966 United Kingdom ............ 14266/66
Mar. 31, 1966 United Kingdom ............ 14267/66

[51] Int. Cl.² .................... A01N 9/36; C07D 239/24
[52] U.S. Cl. .................................. 424/200; 544/123; 260/256.4 N; 260/256.5 R
[58] Field of Search ............... 424/200; 260/256.4 N, 260/256.5 R

[56] References Cited

U.S. PATENT DOCUMENTS

| | | |
|---|---|---|
| 3,287,453 | 11/1966 | McHattie .................. 260/256.5 R |
| 3,651,224 | 3/1972 | Sharpe et al. ................. 424/200 |
| 3,657,247 | 4/1972 | Freeman et al. ............. 260/256.5 R |
| 3,906,094 | 9/1975 | Snell ................................ 424/200 |

*Primary Examiner*—Leonard Schenkman
*Attorney, Agent, or Firm*—Cushman, Darby & Cushman

[57] ABSTRACT

A method and composition are provided for combating fungus of plants wherein there is applied to the fungus a biologically-active pyrimidine derivative having the formula:

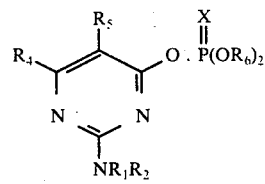

or salt thereof, wherein X is an atom of oxygen or sulphur; $R_1$ is hydrogen; $R_2$ is hydrogen, alkyl or alkenyl containing not more than 6 carbon atoms; phenyl or halo- or alkyl-substituted phenyl, cyclohexyl or acetyl; $R_4$ is alkyl containing not more than 6 carbon atoms or a phenyl radical; $R_5$ is hydrogen, or alkyl or alkenyl containing not more than 6 carbon atoms; $R_6$ is alkyl containing not more than 6 carbon atoms or phenyl.

10 Claims, No Drawings

FUNGICIDAL PYRIMIDINE DERIVATIVES

This is a division of application Ser. No. 114,079, filed Feb. 9, 1971, now U.S. Pat. No. 3,906,094, said Ser. No. 114,079 being a continuation-in-part of Ser. No. 624,126, filed Mar. 20, 1967, now abandoned.

This invention relates to biologically-active compositions containing as an active ingredient a pyrimidine derivative, to new pyrimidine derivatives, to processes for making new pyrimidine derivatives and to methods for combating plant and animal pests.

McHattie, in U.S. Pat. No. 3,287,453, discloses pyrimidine derivatives of the formula:

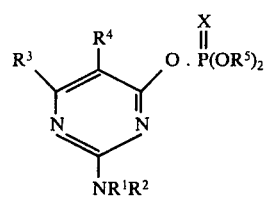

wherein $R^1$, $R^2$ and $R^5$, which may be the same or different, stand for alkyl or alkenyl radicals of not more than 6 carbon atoms, or wherein $R^1$ and $R^2$ together with the adjacent nitrogen atom form a heterocyclic radical, wherein $R^3$ and $R^4$ stand for hydrogen or alkyl or alkenyl radicals of not more than 6 carbon atoms, and wherein X stands for the oxygen or sulphur atom.

McHattie teaches that some of the compounds possess insecticidal properties and some of them possess fungicidal properties.

The compounds which possess insecticidal properties are shown to be those wherein $R^4$ in the formula above stands for a hydrogen atom, whereas the only compound shown to possess fungicidal properties is characterised by the presence of an n-butyl group at $R^4$. Furthermore the fungicidal activity is only demonstrated in the control of one disease, powdery mildew of cucumbers.

We have discovered that if the nature of the substitute of the compounds disclosed by McHattie in U.S. Pat. No. 3,287,453 is changed, then the resultant compounds are unexpectedly and remarkably more effective as insecticides and fungicides than the McHattie compounds.

According to the invention we provide a biologically-active composition comprising as active ingredient a pyrimidine derivative having the formula:

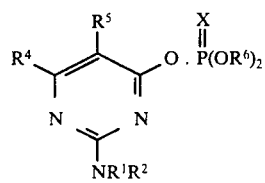

or a salt thereof, wherein either (i) X is an atom of oxygen or sulphur; $R^1$ is hydrogen; $R^2$ is hydrogen, alkyl, alkenyl, unsubstituted or substituted aryl, cycloalkyl, lower acyl or nitrogen-containing heterocyclic radical; $R^4$ and $R^5$, which may be the same or different, are hydrogen, alkyl, alkenyl or substituted or unsubstituted aryl, and $R^6$ is alkyl, alkenyl or aryl; or (ii) X is an atom of oxygen or sulphur; $R^1$ and $R^2$, which may be the same or different, are alkyl, or alkenyl radicals, or together with the adjacent nitrogen atom form a substituted or unsubstituted heterocyclic radical; $R^4$ is an unsubstituted or substituted aryl radical; $R^5$ is hydrogen, or a substituted or unsubstituted alkyl or alkenyl radical; and $R^6$ is a substituted or unsubstituted alkyl or alkenyl radical; and a carrier for the active ingredient comprising a solid diluent, or a liquid diluent containing a wetting agent.

With reference to (i) above, conveniently when $R^2$, $R^4$ and/or $R^5$ are alkyl or alkenyl, they contain not more than six carbon atoms and when $R^6$ is alkyl or alkenyl it contains not more than four carbon atoms. Conveniently, when $R^2$ is an aryl radical it may be a phenyl radical and when substituted the substituents may be alkyl or halogen and when $R^4$ is a aryl radical it may be a phenyl radical.

With reference to (ii) above conveniently, $R^1$ and $R^2$ contain not more than six carbon atoms, $R^4$ is a pheny radical, $R^5$ is hydrogen or a lower alky or alkenyl radical containing not more than six carbon atoms and $R^6$ is an alkyl radical which contains not more than four carbon atoms. The group $NR^1R^2$ preferably stands for a heterocyclic radical, for example, a heterocyclic radical containing a 5- or 6-membered ring, for example the piperidino or morpholino radical.

More particularly, therefore, the invention provides a biologically active composition comprising as active ingredient a pyrimidine derivative of the formula:

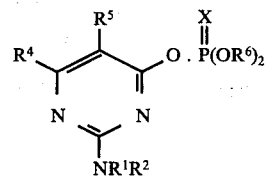

or a salt thereof, wherein X is an atom of oxygen or sulphur; $R^1$ is hydrogen; $R^2$ is hydrogen, alkyl or alkenyl containing not more than six carbon atoms; phenyl or halo- or alkyl- substituted phenyl, cyclohexyl, acetyl, or a nitrogen-containing heterocyclic radical; $R^4$ is alkyl containing not more than six carbon atoms or a phenyl radical; $R^5$ is hydrogen, or alkyl or alkenyl containing not more than six carbon atoms; $R^6$ is alkyl containing not more than six carbon atoms or phenyl; and a carrier for the active ingredient comprising a solid diluent, or a liquid diluent containing a wetting agent.

Specific pyrimidine derivatives according to the invention are listed in Table I below and all the compounds, except those marked with an asterisk, are new compounds.

TABLE I

| Compound No. | NR¹R² | R⁴ | R⁵ | —O P(X)(OR⁶)₂ |
|---|---|---|---|---|
| 1 | —NH—C₆H₅ | CH₃ | H | O . P(S)(OC₂H₅)₂ |
| *2 | —NH₂ | CH₃ | H | O . P(S)(OC₂H₅)₂ |
| 3 | —NH . CH(CH₃)₂ | CH₃ | H | O . P(O)(OC₂H₅)₂ |
| 4 | —NH . C₄H₉n | CH₃ | H | O . P(S)(OC₂H₅)₂ |
| 5 | —NH . CH(CH₃)₂ | CH₃ | H | O . P(S)(OC₂H₅)₂ |
| 6 | —NH . C₆H₄ . CH₃(o) | CH₃ | H | O . P(S)(OC₂H₅)₂ |
| 7 | —NH . C₆H₄ . CH₃(o) | CH₃ | H | O . P(O)(OC₂H₅)₂ |
| 8 | —NH . C₆H₄ . Br(p) | CH₃ | H | O . P(O)(OC₂H₅)₂ |
| 9 | —NH . C₆H₄ . Br(p) | CH₃ | H | O . P(S)(OC₂H₅)₂ |
| 10 | —NH . C₄H₉n | CH₃ | H | O . P(S)(OCH₃)₂ |
| *11 | —NH₂ | CH₃ | H | O . P(O)(OC₂H₅)₂ |
| 12 | —NH . C₆H₄ . CH₃(m) | CH₃ | H | O . P(S)(OC₂H₅)₂ |
| 13 | —NH . C₆H₄ . CH₃(m) | CH₃ | H | O . P(O)(OC₂H₅)₂ |
| 14 | —NH₂ | CH₃ | H | O . P(S)(OCH₃)₂ |
| *15 | —NH₂ | CH₃ | H | O . P(O)(OC₄H₉n)₂ |
| 16 | —NH . CO . CH₃ | CH₃ | H | O . P(O)(OC₂H₅)₂ |
| 17 | —NH₂ | CH₃ | nC₄H₉ | O . P(O)(OC₂H₅)₂ |
| 18 | —NH₂ | CH₃ | nC₄H₉ | O . P(S)(OC₂H₅)₂ |
| 19 | —NH₂ | CH₃ | nC₄H₉ | O . P(O)(OC₄H₉n)₂ |
| 20 | —NH-(2-pyridyl) | CH₃ | H | O . P(O)(OC₂H₅)₂ |
| 21 | —NH₂ | CH₃ | CH₃ | O . P(O)(OC₄H₉n)₂ |
| 22 | —NH₂ | CH₃ | C₂H₅ | O . P(O)(OC₄H₉n)₂ |
| 23 | —NH₂ | C₆H₅ | H | O . P(O)(OC₄H₉n)₂ |
| 24 | —NH₂ | CH₃ | CH₃ | O . P(S)(OC₂H₅)₂ |
| 25 | —NH . CO . CH₃ | CH₃ | H | O . P(S)(OC₂H₅)₂ |
| 26 | —NH . OC . CH₃ | CH₃ | H | O . P(S)(OCH₃)₂ |
| 27 | —NHC₂H₅ | H | H | O . P(O)(OC₂H₅)₂ |
| 28 | —NH₂ | nC₃H₇ | H | O . P(S)(OC₂H₅)₂ |
| 29 | —NH₂ | CH₃ | CH₂=CH—CH₂ | O . P(S)(OC₂H₅)₂ |
| 30 | —NHC₂H₅ | CH₃ | nC₄H₉ | O . P(O)(O—C₆H₅)₂ |
| 31 | —N(morpholino) | C₆H₅ | H | O . P(S)(OC₂H₅)₂ |
| 32 | —N(piperidino) | C₆H₅ | H | O . P(S)(OC₂H₅)₂ |
| 33 | —N(CH₃)₂ | C₆H₅ | H | O . P(O)(OC₂H₅)₂ |
| 34 | —N(4-methylpiperazino) | C₆H₅ | H | O . P(S)(OC₂H₅)₂ |
| 35 | —N(4-methylpiperazino) | C₆H₅ | H | O . P(O)(OC₂H₅)₂ |
| 36 | —N(CH₃)₂ | C₆H₅ | C₂H₅ | O . P(S)(OC₂H₅)₂ |
| 37 | —N(CH₃)₂ | C₆H₅ | CH₂=CH—CH₂ | O . P(S)(OC₂H₅)₂ |

In this specification the numbering of the pyrimidine ring is as follows:

It may be noted that the 4- and 6- positions are equivalent.

As suitable salts of the pyrimidine derivatives of this invention there may be mentioned, for example, the hydrochlorides.

Particularly useful pyrimidine derivatives are those numbered 3, 4, 8, 10, 16, 25, 27, 28, 30, 33 and 34 in Table I above.

The pyrimidine derivatives of the present invention are very toxic towards a variety of invertibrates including molluscs, mosquitoes, mosquito larvae (*Aedes aegypti*), black aphids (*Aphis fabae*), green aphids (*Macrosiphum pisi*), red spider mites (*Tetranychus telarius*), cotton stainer capsids (*Dysdercus fasciatus*), diamond back moth caterpillars (*Plutella maculipennis*), mustard beetles (*Phaedon cochleariae*), common houseflies (*Musca domestica*) and root knot nematodes (*Meloidogyne incognita*). Furthermore, the pyrimidine derivatives of the invention have insecticidal action against insects that prey on animals, for example *Lucilia sericata* (sheep blow flies).

The pyrimidine derivatives of the invention also possess activity against a wide variety of fungal diseases including, for example, the following specific diseases:

*Puccinia recondita* (rust) on wheat
*Phytophthora infestans* (late blight) on tomatoes
*Sphaerotheca fuliginea* (powdery mildew) on cucumber
*Eryaiphe graminis* (powdery mildew) on wheat and barley
*Podosphaera leucotricha* (powdery mildew) on apple
*Uncinula necator* (powdery mildew) on vine
*Plasmopara viticola* (downy mildew) on vine
*Piricularia oryzae* (blast) on rice
*Venturia inaequais* (scab) on apple A particularly useful feature of the activity of the pyrimidine derivatives listed above is their systemic effect, that is to say, their ability to move throughout a plant to reach any part thereof and to combat any insect infestation or fungal infection thereon; it is possible with their use therefore to produce a composition which has valuable systemic insecticidal and fungicidal activity.

In use, pyrimidine derivative of the invention or a composition contaning the same may be applied in a number of ways. Thus their application can suitably be directed onto the foliage of a plant or to infected and/or infested areas thereof; alternatively the soil surrounding a plant, or soil in which seeds or plants are to be sown or planted can be treated with pyrimidine derivative or composition containing the same. If desired, the seeds themselves can be similarly treated. A pyrimidine derivative of this invention or a composition containing the same, may also be used to treat surfaces, for example in dwellings, to render them toxic towards pests. In veterinary usage, a pyrimidine derivative or composition containing the same, may conveniently be administered to any animal for the purpose of combating an insect infestation.

According to a further feature of the invention, therefore, we provide a method of combating undesired plant pests which comprises applying to the locus of the plant a biologically active composition as hereinbefore defined or a novel pyrimidine derivative as hereinafter defined.

In a further aspect of the invention we provide a method of combating undesired insect infestations in animals which comprises administering to an animal a biologically active composition as hereinbefore defined or a novel pyrimidine derivative as hereinafter defined.

The invention further includes a method of combating plant pests which comprises applying to a plant or to seeds thereof a biologically active composition as hereinbefore defined or a novel pyrimidine as hereinafter defined.

In yet a further aspect of the invention, therefore, we provide a method of treating agricultural soil comprising applying to the soil a biologically active composition as hereinbefore defined or a novel pyrimidine derivative as hereinafter defined.

The pyrimidine derivatives and compositions of the invention may be used for agricultural, horticultural or veterinary purposes and the derivative or type of composition used in any instance will depend upon the particular purpose for which it is to be used.

Compositions comprising the invention compounds may be in the form of dusting powders or granules wherein the active ingredient is mixed with a solid diluent or carrier. Suitable solid diluents or carriers may be, for example, kaolin, pumice, bentonite, kieselguhr, dolomite, calcium carbonate, talc, powdered magnesia, Fuller's earth, gypsum, Hewitt's earth, distomaceous earth and China clay. Compositions for dressing seed, for examle, may comprise an agent assisting the adhesion of the composition to the seed, for example, a mineral oil, or a vegetable oil such as castor oil.

The compositions may also be in the form of dispersible powders or grains comprising, in addition to the active ingredient, a wetting agent to facilitate the dispersion of the powder or grains in liquids. Such powders or grains may include fillers, suspending agents and the like.

The compositions may also be in the form of liquid preparations to be used as dips or sprays which are generally aqueous dispersions or emulsions containing the active ingredient in the presence of one or more wetting agents, dispersing agents, emulsifying agents or suspending agents.

Wetting agents, dispersing agents and emulsifying agents may be of the cationic, anionic or non-ionic type. Suitable agents of the cationic type include, for example, quaternary ammonium compounds, for example, cetyltrimethylammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, butyl-naphthalene sulphonate, and a mixture of the sodium salts of diisopropyl- and triisopropyl- naphthalene sulphonic acids. Suitable agents of the non-ionic type include, for example, the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins.

Suitable suspending agents are, for example, hydrophilic colloids, for example polyvinylpyrrolidone and sodium carboxymethylcellulose, and the vegetable gums, for example gum acacia and gum tragacanth, and bentonite.

The aqueous dispersions or emulsions may be prepared by dissolving the active ingredient or ingredients in an organic solvent which may contain one or more wetting, dispersing or emulsifying agents and then adding the mixture so obtained to water which may likewise contain one or more wetting, dispersing or emulsifying agents. Suitable organic solvents are ethylene dichlorde, isopropyl alcohol, propylene glycol, diacetone alcohol, toluene, kerosene, methylnaphthalene, xylenes, trichloroethylene, methyl chloroform and trimethyl-benzene.

The compositions to be used as sprays may also be in the form of aerosols wherein the formulation is held in a container under pressure in the presence of a propellant such as fluorotrichloromethane or dichlorodifluoromethane.

By the inclusion of suitable additives, for example for improving the distribution, adhesive power and resistance to rain on treated surfaces the different compositions can be better adapted for the various uses for which they are intended.

The pyrimidine derivatives may also be conveniently formulated by admixing them with fertilizers. A preferred composition of this type comprises granules of fertilizer material incorporating, for example coated with, a pyrimidine derivative. The fertilizer material, may for example comprise nitrogen or phosphate-containing substances.

In yet a further aspect of the invention, therefore, we provide a fertilizer comprising a pyrimidine derivative as hereinafter defined.

The compositions which are to be used in the form of aqueous dispersions of emulsions are generally supplied in the form of a concentraate containing a high proportion of the active ingredient or ingredients, the said concentrate to be diluted with water before use. These concentrates are often required to withstand storage for prolonged periods and after such storage, to be capable of dilution with water in order to form aqueous preparations which remain homogeneous for a sufficient time to enable them to be applied by conventional spray equipment. The concentrates may convenienty contain from 10-85% by weight of the active ingredient or ingredients and generally from 25-60% by weight of the active ingredient or ingredients. When diluted to form aqueous preparations, such preparations may contain varying amounts of the active ingredient or ingredients depending upon the purpose for which they are to be used, but an aqueous preparation containing between 0.001% and 1.0% by weight of active ingredient or ingredients may be used.

It is to be understood that the pesticidal compositions of this invention may comprise, in addition to a pyrimidine derivative, one or more other compounds having biological activity.

When used for veterinary purposes, the compositions may be in the form of dips, sprays or dusting powders for external application and the compositions described above are suitable for this purpose. The veterinary compositions for external application may also be in the form of a hand dressing prepared from an ointment or cream base, for example white petroleum jelly.

Alternatively, the veterinary compositions of the invention may be in a form suitable for oral administration, for example as tablets, capsules, boluses, suspensions, emulsions or solutions. The compositions for oral administration may contain conventional excipients, for example inert carriers, for example calcium phosphate, lubricating agents, for example magnesium stearate, and granulating and disintegrating agents conventionally used in tablet manufacture, for example starch and/or vegetable gums. The suspensions and emulsions may be prepared using conventional excipients described above.

Alternatively, the veterinary compositions of the invention may be in a form suitable for parenteral administration, for example sterile solutions, suspensions or emulsions. The compositions for parenteral administration may contain conventional excipients, for example solvents, for example water, vegetable oils, or N,N-dimethylacetamide, and excipients described above conventionally used in the preparation of emulsions and suspensions.

The veterinary compositions of the invention may optionally additionally contain one or more substances of known veterinary utility, for example anthelmintics and/or bactericides. Both the veterinary and agricultural compositions of the invention may in addition be stabilised by the incorporation therein of stabilising agents, for example epoxides, for example epichlorohydrin.

It is to be understood that the pesticidal compositions of this invention may comprise, in addition to a pyrimidine derivative, one or more other compounds having biological activity.

Compositions according to the invention were made up in the following manner and tested against various fungal diseases, and the results of these tests are shown in Tables II to IV hereinafter. In the tests, both a protectant and an eradicant test were carried out, and in the protectant test the plants were sprayed so that the leaves were wetted with a solution or suspension containing 500 parts per million of the active compound and 0.1% of a wetting agent, and after 24 hours were inoculated with the disease, the extent of which was assessed visually at the end of the test. In the eradicant test, the plants were inoculated with the disease and then sprayed (so that the leaves were wetted) after a number of days depending on the disease with a solution or suspension containing 500 parts per million of the active compound and 0.1% of a wetting agent. The results are shown in Tables II to IV as a grading giving the percentage amount of disease as follows:

| Grading | Percentage Amount of Disease |
|---------|------------------------------|
| 0 | 61 to 100 |
| 1 | 26 to 60 |
| 2 | 6 to 25 |
| 3 | 0 to 5 |

In the tables the first column indicates the pyrimidine derivative used with reference to the numbers in the first column in Table I above. Each of the subsequent columns in the Table indicates the disease, the host plant, the duration of the test in days and the protectant (PROT) and eradicant (ERAD) results.

TABLE II

| Compound No. | Erysiphe cichoracearum Powdery mildew cucumber 10 days Prot | Erysiphe cichoracearum Powdery mildew cucumber 10 days Erad | Phytopthora infestans Late blight tomato 4 days Prot | Puccinia recondita Rust wheat 10 days Prot | Puccinia recondita Rust wheat 10 days Erad | Plasmopara Viticola Downy mildew vine 7 days Prot | Uncinula necator Powdery mildew vine 14 days Prot | Erysiphe graminis Powdery mildew wheat 10 days Prot |
| --- | --- | --- | --- | --- | --- | --- | --- | --- |
| 1 | 0 | 2 | — | — | — | 0 | 3 | 3 |
| 2 | 0 | 0 | 2 | 0 | 0 | 0 | — | — |
| 3 | 0 | 0 | 0 | 0 | 0 | 1 | 0 | 0 |
| 4 | 1 | 1 | 0 - 1 | 1 | 0 | 2 | 3 | 2 |
| 5 | 2 | 0 | 0 - 1 | 0 | 0 | 1 | 3 | 0 |
| 6 | 0 | 0 | 2 | 3 | 0 | 0 | 0 | 0 |
| 7 | 0 | 0 | 0 - 1 | 0 | 0 | 0 | 0 | 3 |
| 8 | 0 | 0 | 0 - 1 | 2 | 0 | 0 | 0 | 0 |
| 9 | 0 | 0 | 0 | 0 | 0 | 1 | 0 | 2 |
| 10 | 0 | 1 | 0 | 0 | 0 | 1 | 2 | 1 |
| 11 | 0 | 1 | 1 - 2 | 0 | 0 | 0 | — | — |
| 12 | 0 | 0 | 1 | 0 - 1 | 0 | 1 | 0 | 3 |
| 13 | 0 | 1 | 0 - 2 | 3 | 0 | 0 | 0 | 1 |
| 14 | 0 | 0 | 0 - 1 | 0 | 0 | — | — | — |
| 15 | 0 | 0 | 2 | 1 | 0 | 1 | 1 | 0 |
| 16 | 0 | 0 | 2 | 0 | 0 | 0 | — | — |

TABLE III

| Compound No. | Erysiphe* cichoracearum Powdery mildew cucumber 10 days Prot | Erysiphe* cichoracearum Powdery mildew cucumber 10 days Erad | Phytophthora infestans Late blight tomato 4 days Prot | Puccinia recondita Rust wheat 10 days Prot | Puccinia recondita Rust wheat 10 days Erad | Plasmopara viticola Downy mildew vine 7 days Prot | Uncinula necator Powdery mildew vine 14 days Prot | Erysiphe graminis Powdery mildew wheat 10 days Prot |
| --- | --- | --- | --- | --- | --- | --- | --- | --- |
| 17 | 0 | 1 | 0 - 1 | 0 | 0 | 0 | — | 3 |
| 18 | 3 | 0 | 0 | 0 | 0 | 0 | — | — |
| 19 | 0 | 0 | 0 - 1 | 1 | 0 | 1 | 0 | 3 |
| 20 | 0 | 0 | 1 - 3 | 0 | 0 | 0 | — | — |
| 21 | 0 | 1 | 1 | 0 | 0 | 1 | 2 | 0 |
| 22 | 0 | 0 | 1 - 3 | — | 2 | 2 | 1 | 0 |
| 23 | 0 | 1 | 1 - 2 | 1 | 0 | 2 | 0 | 0 |
| 24 | 0 | 0 | 2 | 1 | 0 | 2 | 0 | 0 |
| 25 | 0 | 1 | 2 | 2 | 0 | — | 0 | 3 |
| 26 | 0 | 0 | 0 | 0 | 0 | 0 | 0 | 1 |
| 28 | — | 0 | 1 | 1 | 0 | 1 | 1 | 2 |
| 29 | 0 | 0 | 0 | 0 | 0 | 2 | 0 | 1 |
| 30 | 3 | 3 | 0 | 0 | 0 | — | — | — |
| 31 | 1 | 0 | — | — | — | 3 | 0 | 0 |
| 32 | 1 | 0 | — | — | — | — | — | 0 |
| 33 | — | — | 0 | 1 | 0 | 2 | 0 | 0 |
| 34 | 0 | 1 | 1 | 0 | 0 | 0 | 0 | 0 |
| 35 | 0 | 1 | 0 | 0 | 0 | 0 | 0 | 0 |

*For compounds 24 to 30 the disease was *Sphaerotheoa fuliginea*

TABLE IV

| Compound No. | Erysiphe graminis Powdery mildew Barley 10 days Prot | Podosphaera leucotricha Powdery mildew Apple 7-14 days Prot | Piricularia oryzae Blast Rice 7 days Prot | Venturia inaequalis Scab Apple 14 days Prot |
| --- | --- | --- | --- | --- |
| 1 | — | 2 | — | — |
| 2 | — | 3 | — | — |
| 24 | 3 | 0 | 0 | 0 |
| 25 | 3 | — | — | 3 |
| 26 | 0 | 0 | 0 | 1 |
| 28 | 3 | 0 | 3 | 3 |
| 29 | 3 | 1 | — | 0 |

The toxicity of a number of the compounds of this invention towards a variety of insect pests was investigated and the tests conducted and results obtained are set out below. The compounds of the invention were in each case used in the form of a liquid preparation containing 0.1% by weight of the compound. The preparations were made by dissolving each of the compounds in a mixture of solvents consisting of four parts by volume of acetone and one part by volume of diacetone alcohol. The solutions were then diluted with water containing 0.01% by weight of a wetting agent sold under the trade name of "LISSAPOL" NX until the liquid preparations contained the required concentration of the compound ("LISSAPOL" is a Trade Mark).

The test procedure adopted with regard to each test insect was basically the same and comprised supporting a number of the insects on some medium which may be a host plant or some foodstuff on which the insect feeds, and treating either or both the insect and the medium with the preparations. The mortality of the insects was then assessed at period varying from one to three days after the treatment.

The results of the tests are given below in Table V to VII. In these Tables the first column indicates the compound used. Each of the subsequent columns indicates the name of the test insect, the host plant or medium on which it was supported, and the number of days which were allowed to elapse after treatment before assessing the percentage of insects which had been killed. The assessment is expressed in integers which range from 0 to 3.

0 represents less than 30% kill
1 represents from 30 - 49% kill concentration of the invention compound in the solution used was 100 parts per million.

TABLE V

| Compound No. | Aedes aegypti Mosquito Water — | Aphis fabae Black aphid Broad bean 2 days | Macrosiphum pisi Green aphid Broad bean 2 days | Tetranychus telarius Red spider mite French bean 3 days | Tetranychus telarius Red spider egg French bean 3 days | Dysdercus fasciatus Cotton stained capsid Cotton 3 days | Plutella maculipennis Diamond back moth caterpillar Cabbage/paper 2 days | Calandra granaria Grain weevil Wheat grain 3 days | Phaedon cochleariae Mustard beetle Mustard/paper 2 days | Musca domestica House-fly Milk & sugar Cotton wool 1 day |
|---|---|---|---|---|---|---|---|---|---|---|
| 1 | 3 | 3 | 3 | 3 | 3 | 3 | 0 | 3 | 3 | 3 |
| 2 | 3 | 3 | 3 | 3 | 3 | — | — | — | — | — |
| 3 | 3 | 3 | 3 | 3 | 3 | 3 | 3 | 3 | 3 | 3 |
| 4 | 3 | 3 | 3 | 3 | 3 | 3 | 3 | 3 | 3 | 3 |
| 5 | 3 | 3 | 3 | 3 | 3 | 3 | 3 | 1 | 3 | 2 |
| 6 | 3 | 3 | 3 | 3 | 3 | 3 | 3 | 2 | 3 | 3 |
| 7 | 3 | 3 | 3 | 3 | 0 | 2 | 3 | 2 | 3 | 3 |
| 8 | 3 | 3 | 3 | 3 | 3 | 3 | 3 | 3 | 3 | 3 |
| 9 | 3 | 1 | 2 | 3 | 3 | 3 | 3 | 3 | 3 | 3 |
| 10 | 3 | 3 | 3 | 3 | 3 | 3 | 3 | 3 | 3 | 3 |
| 11 | 3 | 3 | 3 | 3 | 3 | 3 | 3 | 3 | 3 | 3 |
| 12 | 3 | 3 | 3 | 3 | 0 | 3 | 3 | 2 | 0 | 3 | 0 |
| 13 | 3 | 3 | 3 | 3 | 3 | 3 | 0 | 0 | 0 | 0 |
| 14 | 3 | 3 | 3 | 3 | 3 | 3 | — | 3 | 3 | 3 |
| 15 | 3 | 0 | 1 | 3 | 0 | 3 | 0 | 0 | 3 | 3 |
| 16 | 3 | 3 | 3 | 3 | 3 | 3 | 3 | 3 | 3 | 3 |
| 17 | 3 | 3 | 3 | 3 | 0 | 0 | 0 | 0 | 0 | 0 |
| 18 | 3 | 3 | 3 | 3 | 0 | 1 | 0 | 0 | 1 | 0 |
| 19 | 3 | 2 | 3 | 3 | 0 | 0 | 0 | 0 | 0 | 0 |
| 20 | 0 | 0 | 3 | 0 | 0 | 0 | 0 | 0 | 0 | 0 |
| 21 | 3 | 3 | 3 | — | 0 | 0 | 0 | 0 | 2 | 0 |
| 22 | 0 | 1 | 1 | 3 | 0 | — | — | — | — | — |
| 23 | 3 | 0 | 0 | 0 | 0 | 0 | 0 | 0 | 1 | 3 |

TABLE VI

| Compound No. | Aedes Aegypta Mosquito larva Water — | Aphis fabae Black aphid Broad bean 2 days | Macrosiphum pisi Green aphid Broad bean 2 days | Tetranychus telarius Red spider mite French bean 3 days | Tetranychus telarius Red spider egg French bean 3 days | Dysdercus fasciatus Cotton stainer capsid Cotton 3 days | Plutella maculipennis Diamond back moth caterpillar Cabbage/paper 2 days | Calandra granaria Grain weevil Wheat grain 3 days | Phaedon cochleariae Mustard beetle Mustard/paper 2 days | Musca domestica House-fly Milk & sugar cotton wool 1 day |
|---|---|---|---|---|---|---|---|---|---|---|
| 25 | 3 | 3 | 3 | 3 | 3 | 3 | 3 | 3 | 3 | 3 |
| 26 | 3 | 3 | 3 | 3 | 0 | 0 | 0 | 0 | 0 | 0 |
| 27 | 3 | 3 | 3 | 3 | 2 | 3 | 3 | 3 | 3 | 3 |
| 28 | 3 | 3 | 3 | 3 | 3 | 1 | 3 | 0 | 3 | 3 |
| 29 | 3 | 2 | 2 | 3 | 0 | 0 | 0 | 0 | 0 | 0 |

In addition to the above activity compounds 26 and 27 gave a grading of 3 against the pest Meloidogyne incognita (Root knot nematode) after 2 days.

TABLE VII

| Compound No. | Aedes aegypti Mosquito larva Water — | Aphia fabae Black aphid Broad bean 2 days | Macrosiphum pisi Green aphid Broad bean 2 days | Tetrancychus telarius Red spider mite French bean 3 days | Tetranychus telarius Red spider egg French bean 3 days | Dysdercus fasciatus Cotton stainer capsid Cotton 3 days | Plutella maculipennis Diamond back moth caterpillar Cabbage/paper 2 days | Calandra granaria Grain weevil Wheat grain 3 days | Phaedon cochleariae Mustard beetle Mustard/paper 2 days | Musca domestica House-fly Milk & sugar cotton wool 1 day |
|---|---|---|---|---|---|---|---|---|---|---|
| 31 | 3 | 3 | 3 | 3 | 3 | 1 | 0 | 0 | 3 | 3 |
| 32 | 3 | 2 | 2 | 3 | 0 | 2 | 2 | 0 | 0 | 0 |
| 33 | 3 | 3 | 3 | 3 | 3 | 3 | 3 | 3 | 3 | 3 |
| 34 | 3 | 0 | 0 | 3 | 0 | 0 | 0 | 0 | 2 | 2 |

2 represents from 50 - 90% kill
3 represents over 90% kill

The concentration of the invention compound in the solutions used was 1,000 parts per million for all the pests except in the cases of *Aedes aegypta* (Tables V to VII) and *Meloidogyne incognita* (Table VI) when the According to a further feature of the invention we provide novel pyrimidine derivatives of the formula:

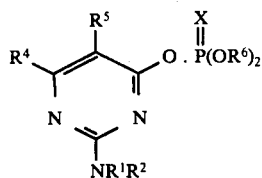

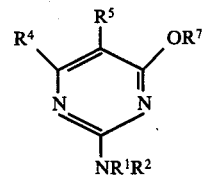

or a salt thereof, wherein either (i) X is an atom of oxygen or sulphur; $R^1$ is hydrogen; $R^2$ is hydrogen, alkyl, alkenyl, unsubstituted or substituted aryl, cycloalkyl, lower acyl or nitrogen-containing heterocyclic radical; $R^4$ and $R^5$, which may be the same or different, are hydrogen, alkyl, alkenyl or substituted or unsubstituted aryl, and $R^6$ is alkyl, alkenyl or aryl; provided that $R^1$, $R^2$ and $R^5$ are not all hydrogen; or (ii) X is an atom of oxygen or sulphur; $R^1$ and $R^2$, which may be the same or different, are alkyl or alkenyl radicals, or together with the adjacent nitrogen atom form a substituted or unsubstituted heterocyclic radical; $R^4$ is an unsubstituted or substituted aryl radical; $R^5$ is hydrogen, or a substituted or unsubstituted alkyl or alkenyl radical; and $R^6$ is a substituted or unsubstituted alkyl or alkenyl radical.

With reference to (i) above preferred and particularly useful pyrimidine derivatives are those wherein $R^2$, $R^4$ and/or $R^5$ are alkyl or alkenyl radicals containing not more than six carbon atoms; $R^6$ is an alkyl or alkenyl radical containing not more than four carbon atoms. Conveniently, when $R^2$ is an aryl radical it is a phenyl radical and when substituted preferred substituents are alkyl or halogen.

With refrence to (ii) above preferred and particularly useful pyrimidine derivatives are those wherein $R^1$ and $R^2$ contain not more than six carbon atoms, $R^4$ is a phenyl radical, $R^5$ is hydrogen or a lower alkyl or alkenyl radical contaning not more than six carbon atoms and $R^6$ is an alkyl radical containing not more than four carbon atoms. The group $NR^1R^2$ preferably stands for a heterocyclic radical, for example, a heterocyclic radical containing a 5- or 6- membered ring, for example the piperidino or morpholino radical.

More particularly, therefore, in a further aspect the invention provides a pyrimidine derivative of the formula:

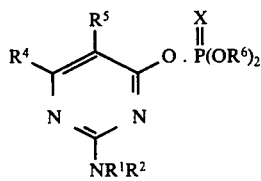

or a salt thereof, wherein X is an atom of oxygen or sulphur; $R^1$ is hydrogen; $R^2$ is hydrogen, alkyl or alkenyl containing not more than six carbon atoms, phenyl or halo- or alkyl- substituted phenyl, cyclohexyl, acetyl, or a nitrogen-containing heterocyclic radical; $R^4$ is alkyl containing not more than six carbon atoms or a phenyl radical; $R^5$ is hydrogen, or alkyl or alkenyl containing not more than six carbon atoms; $R^6$ is alkyl containing not more than six carbon atoms or phenyl.

According to a further feature of the invention, we provide a process for the manufacture of the said novel pyrimidine derivatives which comprises reacting a compound of the formula:

wherein $R^1$, $R^2$, $R^4$ and $R^5$ have the meanings stated and $R^7$ is hydrogen or an alkali metal atom, with a halogen derivative of the formula:

whrein $R^6$ and X have the meanings stated and Y is a halogen atom; if necessary in the presence of a diluent as a reaction medium.

When $R^7$ stands for an alkali metal atom, it may be, for example, a sodium or potassium atom. Conveniently Y is, for example, a chlorine or bromine atom.

In the case where $R^7$ is hydrogen, the starting compound is, conveniently, first converted to the corresponding alkali metal derivative, for example, by reaction with a solution of sodium in ethanol, or the reaction is carried out in the presence of an acid-binding agent, for example, an alkali metal salt of a weak acid, for example, an alkali metal carbonate, for example potassium carbonate, or a tertiary organic base, for example, a trialkylamine of not more than twelve carbon atoms, for example, triethylamine, or an N,N-dialkylarylamine, for example an N,N-dialkylarylamine of not more than twelve carbon atoms, for example N,N-dimethylaniline.

The reaction may conveniently be carried out in an inert diluent or solvent, for example benzene, ethyl acetate, acetone, methyl ethyl ketone, methyl butyl ketone, toluene, acetonitrile, or dimethylformamide and it may be accelerated or completed for example by the application of heat and/or the use of a catalyst.

EXAMPLE 1

The compound O,O-diethyl-O-(2-amino-5-n-butyl-4-methyl-pyrimid-6-yl) phosphorothionate (Compound no. 18, Table I) having the formula:

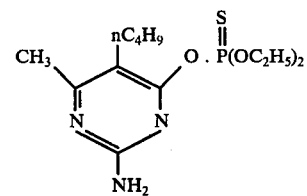

was prepared as follows:

2-Amino-5-n-butyl-4-hydroxy-6-methylpyrimidine (7.24 g., 0.04 mole) was added to sodium (0.92 g., 0.04 mole) in dry ethanol (40 ml.). The solution was kept at 40° C for 30 minutes, the solvent removed in vacuo, and the residue dried by aseotropic distillation with benzene.

To the dry residue was added dry benzene (110 ml.), followed by diethylchlorothiophosphate (0.04 mole), and the mixture stirred and refluxed overnight. The cooled mixture was shaken with ice-cold 5% aqueous sodium hydroxide solution, washed with water until the washings were alkali-free, dried ($Na_2SO_4$) and the benzene removed in vacuo. The residue crystallised on being allowed to stand, and was recrystallised from petroleum ether, 4.5 g., m.p. 79°–80° C.

EXAMPLE 2

The compound O,O-diethyl-O-(2-n-butylamino-4-methyl-pyrimid-6-yl) phosphorothionate (Compound no. 4, Table I) having the formula:

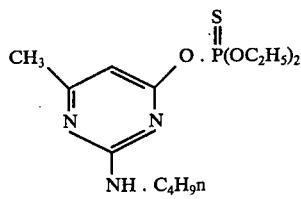

was prepared as follows:

A mixture of 2-n-butylamino-4-hydroxy-6-methylpyrimidine (5 g., 0.028 mole) and anhydrous potassium carbonate (3.82 g., 0.028 mole) in dry enzene (75 ml.) was stirred and refluxed for 3 hours with azeotropic removal of water. To the cooled mixture was added diethylchlorothiophosphate (0.028 mole), and the reaction mixture stirred and refluxed overnight. The cooled mixture was washed with cold 5% aqueous sodium hydroxide solution, and then with water until the washings were alkali-free. The benzene layer was dried ($Na_2SO_4$) and the solvent removed to leave a viscous oil which was heated at 50° C under 0.01 mm. for 20 minutes to leave the product as a colourless oil, 4.8 g., $n_D^{23}$ 1.5217.

EXAMPLE 3

The compound having the formula:

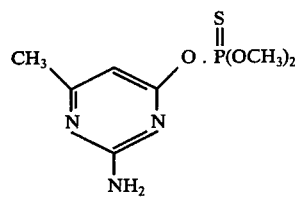

(Compound no. 14, Table I) was prepared as follows:

2-Amino-4-hydroxy-6-methylpyrimidine (5 g., 0.04 mole) was suspended in dry dimethylformamide, and to the suspension was added, in an atmosphere of nitrogen, sodium hydride (1.92 g., of 50% mineral oil suspension 0.04 mole) a little at a time, allowing the exothermic reaction to subside before each subsequent addition. Dimethylchlorothiophosphate (0.42 g., 0.04 mole) was then added dropwise with stirring; the temperature of the reaction mixture rose to 50° C during the addition. The mixture was stirred for 1 hour and then poured into water (400 ml.). The product separated as an oil which soon crystallised, and was filtered off and dried. Recrystallisation from benzene-petroleum ether gave plates (3 g.) m.p. 106°–108° C.

The following compounds of Table I above were prepared in a similar manner to Examples 1, 2 or 3.

| Compound No. | Prepared by method of Example No. | Physical Characteristics of Compound |
|---|---|---|
| 1 | 1 | $n_D^{23}$ 1.5194 |
| 2 | 1 | m.p. 103° C. Recrystallised from benzene/ petroleum ether. |
| 3 | 2 | $n_D^{25}$ 1.5030 |
| 5 | 2 | $n_D^{25}$ 1.5223 |
| 6 | 1 | m.p. 76–78° C. Recrystallised from petroleum ether. |
| 7 | 1 | m.p. 82° C. Recrystallised from benzene/petroleum ether. |
| 8 | 1 | m.p. 118° C. Recrystallised from benzene/petroleum ether. |
| 9 | 1 | $n_D^{25}$ 1.5649 |
| 10 | 2 | Red oil. |
| 11 | 1 | m.p. 110–111° C. Recrystallised from benzene/petroleum ether. |
| 12 | 1 | $n_D^{20}$ 1.5757 |
| 13 | 1 | $n_D^{20}$ 1.5631 |
| 15 | 1 | m.p. 103° C. Recrystallised from benzene/petroleum ether. |
| 16 | 1 | m.p. 96° C. Recrystallised from benzene/petroleum ether. |
| 17 | 1 | m.p. 105–107° C. Recrystallised from 60–80° petroleum ether. |
| 19 | 1 | m.p. 76–78° C. Recrystallised from petroleum ether. |
| 20 | 1 | m.p. 84° C. Recrystallised from petroleum ether. |
| 21 | 1 | m.p. 102° C. Recrystallised from benzene/petroleum ether. |
| 22 | 1 | $n_D^{27}$ 1.4241 |
| 23 | 1 | m.p. 102° C. Recrystallised from petroleum ether. |
| 24 | 3 | m.p. 92° C. Recrystallised from isopropyl alcohol. |
| 25 | 3 | m.p. 74° C. Recrystallised from isopropyl alcohol. |
| 26 | 3 | m.p. 145–150° C. Recrystallised from a mixture of isopropyl alcohol and petroleum ether. |
| 27 | 1 | $n_D^{25}$ 1.4985 |
| 28 | 3 | Viscous liquid (low m.p. solid) |
| 29 | 3 | m.p. 84° C. Recrystallised from petroleum ether. |
| 30 | 1 | $n_D^{23}$ 1.5521 |

EXAMPLE 4

The compound O,O-diethyl-O-(4-phenyl-2-piperidino-pyrimid-6-yl) phosphorothionate, (Compound no. 32 in Table I) having the formula:

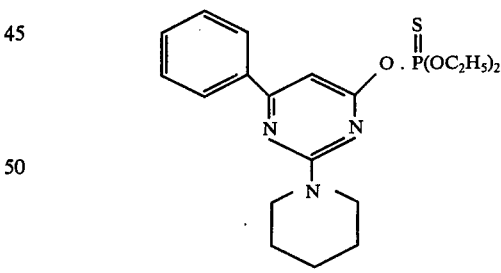

was prepared as follows:

A mixture of 4-hydroxy-6-phenyl-2-piperidinopyrimidine (2.55 g., 0.01 mole), triethylamine (1.01 g., 0.01 mole) and diethylchlorothiophosphate (1.89 g., 0.01 mole) in dry benzene (50 ml.) was refluxed overnight. The mixture was allowed to cool, filtered, and the filtrate washed with ice-cold 5% sodium hydroxide solution, and then with water until the washings were alkali-free, and the benzene layer dried ($Na_2SO_4$). Removal of the solvent gave a viscous oil which crystallised on being allowed to stand. Recrystallisation from petroleum ether (60°–80°) gave the product, m.p. 55° C. (3.2 g., 78%).

EXAMPLE 5

The compound (Compound no. 31 of Table I) having the formula:

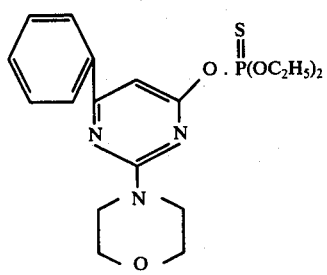

was prepared as follows:

A mixture of 4-hydroxy-2-morpholino-6-phenyl-pyrimidine (5 g., 0.019 mole) and anhydrous potassium carbonate (2.69 g., 0.019 mole) in dry benzene (60 ml.) was stirred and refluxed with azeotropic removal of water for 2 hours. To the cooled mixture was added diethylchlorothiophosphate (3.68 g., 0.019 mole) and the reaction mixture stirred and refluxed for 16 hours. The cooled mixture was washed with cold 5% aqueous sodium hydroxide solution, washed with water until the washings were alkali-free and the benzene layer dried (MgSO$_4$). Removal of the solvent gave the product, recrystallised from petroleum ether, 2 g., m.p. 64°–66° C.

The following compounds of Table I above were prepared in a similar manner to the method used in Example 2.

| Compound No. | Refractive Index |
|---|---|
| 35 | $n_D^{23} = 1.5630$ |
| 36 | $n_D^{19} = 1.5727$ |
| 34 | $n_D^{22} = 1.5753$ |
| 37 | $n_D^{22} = 1.5690$ |
| 33 | $n_D^{25} = 1.5552$ |

EXAMPLE 6

The compound O,O-diethyl-O-(2-dimethylamino-5-ethyl-4-phenylpyrimid-6-yl) phosphorothionate (Compound no. 36, Table I) having the formula:

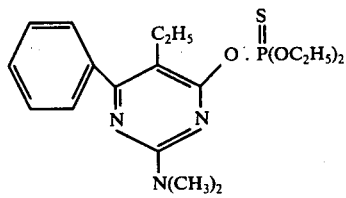

was prepared as follows:

2-Dimethylamino-5-ethyl-4-hydroxy-6-phenylpyrimidine (4.87 g., 0.02 mole) was added to a solution of sodium (0.46 g., 0.02 mole) in dry ethanol (50 ml.). The solution was kept at 40° C for 20 minutes, the solvent removed in vacuo, and the residue dried by azeotropic distillation with benzene. To the dry residue was added dry benzene (50 ml.) followed by diethylchlorothiophosphate (3.3 ml., 0.02 mole) and the mixture was stirred and refluxed overnight. The cooled mixture was shaken with ice-cold 5% aqueous sodium hydroxide solution, washed with water until the washing were alkali-free, dried (Na$_2$SO$_4$) and the benzene removed in vacuo. The residue was heaated at 40° C under 0.01 mm. for 20 minutes to remove volatile materials leaving the product as a pale yellow oil, $n_D^{19}$ 1.5727, 4.3 g.

EXAMPLE 7

This example illustrates a concentrate comprising a miscible oil which is readily convertible by dilution with water into a liquid preparation suitable for spraying purposes. The concentrate has the following composition:

| | % wt. |
|---|---|
| Compound No. 6 (Table I) | 25.0 |
| "LUBROL" L (alkylphenol/ethylene oxide condensate; "LUBROL" is a Trade Mark) | 2.5 |
| Calcium dodecylbenzenesulphonate | 2.5 |
| "AROMASOL" H (alkylbenzene solvent; "AROMASOL" is a Trade Mark) | 70.0 |
| | 100.0 |

EXAMPLE 8

This example also illustrates a concentrate which is in the form of a miscible oil. The composition of this concentrate is as follows:

| | % wt. |
|---|---|
| Compound No. 6 (Table I) | 25.0 |
| "LUBROL" L ("LUBROL" is a Trade Mark) | 4.0 |
| Calcium dodecylbenzenesulphonate | 6.0 |
| "AROMASOL" H ("AROMASOL" is a Trade Mark) | 65.0 |
| | 100.0 |

EXAMPLE 9

This example illustrates a wettable powder having the following composition:

| | % wt. |
|---|---|
| Compound No. 6 (Table I) | 25.0 |
| Sodium silicate | 5.0 |
| Calcium lignosulphonate | 5.0 |
| China clay | 65.0 |
| | 100.0 |

EXAMPLE 10

This example illustrates an atomisable fluid comprising a mixture consisting of 25% by weight of the Compound no. 6 (Table I) and 75% by weight of xylene.

EXAMPLE 11

This example illustrates a dusting powder which may be applied directly to plants or other surfaces and comprises 1% by weight of the Compound No. 6 (Table I) and 99% by weight of talc.

EXAMPLE 12

10 Parts by weight of Compound no. 6 (Table I), 10 parts of an ethylene oxide-octylphenol condensate ("LISSAPOL" NX; "LISSAPOL" is a Trade Mark) and 80 parts by weight of diacetone alcohol were thoroughly mixed. There was thus obtained a concentrate which, on mixing with water, gave an aqueous dispersion suitable for application as a spray in the control of insect pests.

EXAMPLE 13

The ingredients listed below were ground together in the proportions stated to produce a powdered mixture readily dispersible in liquids.

|  | % wt. |
|---|---|
| Compound No. 6 (Table I) | 50% |
| "DISPERSOL" T ("DISPERSOL" is a Trade Mark) | 5% |
| China clay | 45% |
|  | 100% |

EXAMPLE 14

A composition suitable for use as a seed dressing was prepared by mixing all three of the ingredients set out below in the proportions stated

|  | wt% |
|---|---|
| Compound No. 6 (Table I) | 80 |
| Mineral oil | 2 |
| China Clay | 18 |
|  | 100% |

EXAMPLE 15

A granular composition was prepared by dissolving the active ingredient in a solvent, spraying the solution obtained onto the granules of pumice and allowing the solvent to evaporate.

|  | wt% |
|---|---|
| Compound No. 6 (Table I) | 5 |
| Pumice granules | 95 |
|  | 100% |

EXAMPLE 16

The compounds numbered 3,4,8,10,16,25,27,28,30,33 and 34 in Table I heretofore were formulated in the same manner as set out in Example numbers 7 to 15 above.

EXAMPLE 17

The following test was used to evaluate the fungicidal activity of compounds disclosed by McHattie in U.S. Pat. No. 3,287,453, in comparison with the invention compounds against four fungal disease of plants.

The McHattie compounds are hereinafter designated as compounds A, B, C, D and E, and have the following formulae:

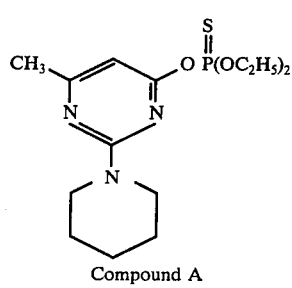

Compound A

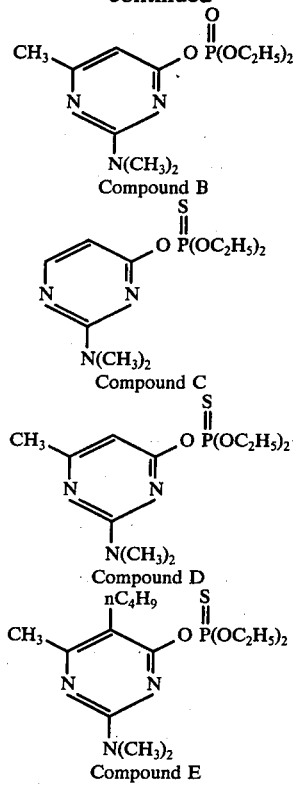

The procedure used was identical to that detailed hereinabove in respect of the invention compounds, except that only the protectant tests were carried out.

The results, graded as hereinabove, are given in the following Tables, one for each disease.

Protectant test against the disease brown rust of wheat

| (Puccinia recondita) | | | |
|---|---|---|---|
| McHattie Compound | Grading | Invention Compound | Grading |
| A | 0 | 6 | 3 |
| B | 0 | 8 | 2 |
| C | 0 | 13 | 3 |
| D | 0 | 25 | 2 |
| E | 1 | | |

Protected test against the disease powdery mildew of cucumbers

| (Erysiphe cichoracearum) | | | |
|---|---|---|---|
| McHattie Compound | Grading | Invention Compound | Grading |
| A | 0 | 5 | 2 |
| B | 0 | 18 | 3 |
| C | 0 | | |
| D | 0 | | |
| E | 3 | | |

Protectant test against the disease late blight of tomatoes

| (Phytophthora infestans) | | | | | |
|---|---|---|---|---|---|
| McHattie Compound | Grading | Invention Compound | Grading | Invention Compound | Grading |
| A | 0 | 2 | 2 | 20 | 3 |
| B | 1 | 6 | 2 | 22 | 3 |
| C | 0 | 11 | 2 | 23 | 2 |

-continued

| (*Phytophthora infestans*) McHattie Compound | Grading | Invention Compound | Grading | Invention Compound | Grading |
|---|---|---|---|---|---|
| D | 0 | 13 | 2 | 24 | 2 |
| E | 0 | 15 | 2 | 25 | 2 |
|   |   | 16 | 2 |   |   |

Protectant test against the disease downy mildew of vines

| (*Plasmopora viticola*) McHattie Compound | Grading | Invention Compound | Grading | Invention Compound | Grading |
|---|---|---|---|---|---|
| A | 0 | 4 | 2 | 29 | 2 |
| B | 0 | 22 | 2 | 31 | 3 |
| C | 0 | 23 | 2 | 33 | 2 |
| D | 0 | 24 | 2 |   |   |
| E | 2 |   |   |   |   |

The above results clearly demonstrate that a high level of fungicidal activity is shown by the invention compounds, and that the McHattie compounds (except compound E) are devoid of any such activity.

EXAMPLE 18

The following procedure was used to evaluate the fungicial activity of the McHattie compound E and the compound No. 5 against the fungal disease *Venturia inaequalis* (apple scab).

An aqueous preparation containing the chemical to be evaluated was prepared by dissolving the chemical in a little diacetone alcohol and diluting the solution thus obtained with water containing 0.1% of a wetting agent until the preparation contained 1000 ppm. (parts per million) of the chemical. Aliquots of this preparation were then further diluted with water to obtain preparations containing 500,125, 25 and 10 ppm. of the chemical.

The preparations were then sprayed onto the foliage of young apple plants to wet the foliage, care being taken to prevent any of the preparation entering the soil in which the apple plants were growing. Two replicates were used for each chemical and for each rate of application.

24 hours later the plants were infected with the disease *Venturia inaequalis*, and after a further period of 21 days, the extent of disease was visually assessed by comparison with untreated plants which had been infected at the same time as the treated plants.

The results of the above evaluation are given in Table A below, wherein the extent of disease is given as a grading from 0 to 3 wherein the grading represents amount of disease expressed as a percentage of the amount of disease in the untreated plants.

| Grading | Percentage Amount of Disease |
|---|---|
| 0 | 61 to 100 |
| 1 | 26 to 60 |
| 2 | 6 to 25 |
| 3 | 0 to 5 |

TABLE A

| Rate of application | Grading | |
|---|---|---|
| of chemical (ppm) | Compound No. 5 | McHattie Compound E |
| 500 | 3 | 3 |
| 125 | 3 | 1 |
| 25 | 3 | 0 |
| 10 | 3 | 0 |

These results demonstrate the superior performance of an invention compound of the present application over the McHattie compound E. This is surprising finding in particular because all the work in this field so far has indicated that chemicals of this type are active only against the powdery mildew disease of apple trees at commercially usable rates of application. Since *Venturia inaequalis* is not a powdery mildew, the unexpected activity of the invention compound against this disease at commercially usable rates of application now renders it feasible to protect apple trees against attacks of both powdery mildew (*Podosphaera leucotricha*) and apple scab (*Venturia inaequalis*) by the application of a single chemical.

EXAMPLE 19

The following procedure was used to evaluate the systemic fungicial activity of the McHattie compound E and the compound no. 30 against the disease *Erysiphe graminis* (powdery mildew of wheat).

Preparations containing 1000, 500, 125, and 25 ppm of the chemical to be evaluated were prepared in the manner described in the previous example.

Wheat seedlings, free from disease, were grown in small pots, there being from 5 to 8 seedlings in each pot. The preparation (10 cc.) was absorbed into the soil in which the seedlings were growing, care being taken to prevent any of the preparation coming in contact with the aerial parts of the plants. Two replicates were used for each chemical and for each rate of application.

After 48 hours the plants were infested with the disease *Erysiphe graminis*, and after a further period of 7 days the extent of disease was visually assessed by comparison with untreated plants which had been infected at the same time as the treated plants.

The results of the evaluation were graded as in the previous example and are given in Table B below.

TABLE B

| Rate of application | Grading | |
|---|---|---|
| of chemical (ppm.) | Compound No.30 | McHattie Compound E |
| 1000 | — | 0 |
| 500 | 3 | 0 |
| 125 | 3 | 0 |
| 25 | 3 | 0 |

The results indicate that a surprising and remarkable degree of control of the disease has been achieved by application to the soil of an invention compound whereas the McHattie compound E has completely failed to control the disease when applied in a similar manner, even at rates considerably in excess of those which would be commercially useful. The control shown by the invention compound is of a systemic nature, an activity not predicted in any way by the McHattie reference, U.S. patent specification No. 3,287,453.

Where in the foregoing specification a chemical structure has been given showing an unsubstituted or monosubstituted amino-pyrimidine a tautomeric structure of an imino pyridine is to be included within the scope of the invention in any case where such tautomerism takes place.

What I claim is:

1. A pyrimidine derivative having the formula:

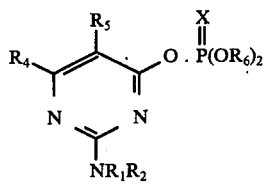

or a salt thereof wherein X is an atom of oxygen or sulphur; $R_1$ is hydrogen; $R_2$ is hydrogen, alkyl containing not more than 6 carbon atoms or alkenyl containing not more than 6 carbon atoms; phenyl or halo- or methyl-substituted phenyl, cyclohexyl or acetyl; $R_4$ is alkyl containing not more than 6 carbon atoms or a phenyl radical; $R_5$ is hydrogen, or alkyl containing not more than 6 carbon atoms or alkenyl containing not more than 6 carbon atoms; $R_6$ is alkyl containing not more than 6 carbon atoms.

2. A pyrimidine derivative according to claim 1 wherein $R_2$ is alkyl; $R_4$ is alkyl and $R_5$ is hydrogen.

3. A pyrimidine derivative according to claim 1 having the formula

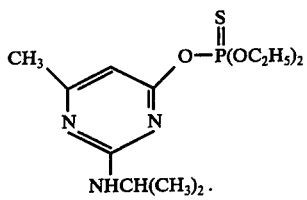

4. A fungicidal composition comprising, as active ingredient, a fungicidally effective amount of a pyrimidine derivative according to claim 1 and a major amount of an inert carrier therefor.

5. A fungicidal composition comprising, as active ingredient, a fungicidally effective amount of a pyrimidine derivative according to claim 2 and a major amount of an inert carrier therefor.

6. A fungicidal composition comprising, as active ingredient, a fungicidally effective amount of a pyrimidine derivative according to claim 3 and a major amount of an inert carrier therefor.

7. A method of combating plant fungus which comprises applying to a plant or to seeds thereof, a fungicidally effective amount of a pyrimidine derivative as defined in claim 1.

8. The method of claim 7 wherein the pyrimidine derivative is one wherein $R_2$ is alkyl; $R_4$ is alkyl and $R_5$ is hydrogen.

9. A method of claim 7 in which the pyrimidine derivative has the formula:

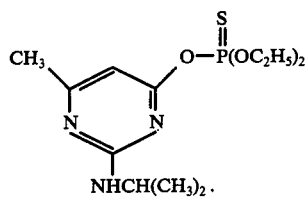

10. A method for treating agricultural soil to combat undesired plant fungus comprising applying to the soil a fungicidally effective amount of a pyrimidine derivative as defined in claim 1.

* * * * *